United States Patent
Lal et al.

(10) Patent No.: US 6,638,249 B1
(45) Date of Patent: Oct. 28, 2003

(54) ULTRASONICALLY ACTUATED NEEDLE PUMP SYSTEM

(75) Inventors: Amit Lal, Madison, WI (US); Chung-Hoon Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 377 days.

(21) Appl. No.: 09/617,478

(22) Filed: Jul. 17, 2000

(51) Int. Cl.$^7$ ................................................ A61M 1/00
(52) U.S. Cl. ...................................................... 604/151
(58) Field of Search .................... 604/151, 152, 604/153, 154, 155, 296; 128/200.14

(56) References Cited

U.S. PATENT DOCUMENTS

| | | | |
|---|---|---|---|
| 4,428,748 A | * 1/1984 | Peyman et al. | 604/22 |
| 4,634,420 A | 1/1987 | Spinosa et al. | |
| 5,311,871 A | 5/1994 | Yock | |
| 5,354,265 A | * 10/1994 | Mackool | 604/22 |
| 5,486,162 A | 1/1996 | Brumbach | |
| 5,562,610 A | 10/1996 | Brumbach | |
| 5,569,968 A | 10/1996 | Lal et al. | |
| 5,582,184 A | 12/1996 | Erickson et al. | |
| 5,656,016 A | * 8/1997 | Ogden | 601/2 |
| 5,674,226 A | * 10/1997 | Doherty et al. | 606/107 |
| 5,682,233 A | 10/1997 | Brinda | |
| 5,728,089 A | 3/1998 | Lal et al. | |
| 5,746,217 A | 5/1998 | Erickson et al. | |
| 5,820,570 A | 10/1998 | Erickson et al. | |
| 5,823,973 A | 10/1998 | Racchini et al. | |
| 5,879,310 A | 3/1999 | Sopp et al. | |
| 5,879,367 A | 3/1999 | Latterell et al. | |
| 6,210,988 B1 | * 4/2001 | Howe et al. | 438/50 |
| 6,224,566 B1 | * 5/2001 | Loeb | 604/22 |
| 6,241,700 B1 | * 6/2001 | Leukanech | 604/19 |
| 6,249,075 B1 | * 6/2001 | Bishop et al. | 310/338 |
| 6,300,706 B1 | * 10/2001 | Grudkowski et al. | 310/334 |
| 6,448,622 B1 | * 9/2002 | Franke et al. | 257/415 |
| 6,475,214 B1 | * 11/2002 | Moaddeb | 606/41 |
| 6,484,052 B1 | * 11/2002 | Visuri et al. | 604/20 |
| 6,490,474 B1 | * 12/2002 | Willis et al. | 600/424 |

FOREIGN PATENT DOCUMENTS

WO     WO 98 00194 A     1/1998

OTHER PUBLICATIONS

Amit Lal, "Micromachined Silicon Ultrasonic Longitudinal Mode Actuators: Theory and Applications to Surgery, Pumping, and Atomization," Ph.D. Dissertation, University of California, Berkeley, 1996, pp. 137–177.

\* cited by examiner

*Primary Examiner*—Daniel Robinson
(74) *Attorney, Agent, or Firm*—Foley & Lardner (57) ABSTRACT

An ultrasonically driven pump, which may be used for sampling body fluids or atomizing liquids, has a stationary outer needle and an inner needle mounted within the bore of the outer needle. The distal end of the inner needle is positioned adjacent to the distal end of the outer needle. The inner needle is ultrasonically vibrated by an ultrasonic actuator without vibrating the outer needle, with resulting draw of liquid through the distal end of the outer needle into the bore of the inner needle for discharge through the proximal end of the inner needle. The outer needle can be formed to have a penetrating tip suited for penetrating the skin of a subject to allow sampling of body fluids including interstitial fluids. The pump can also be used for atomizing liquid, by drawing liquid from a supply that is pumped from the distal end to an open proximal end of the inner needle where the liquid is discharged by atomization into the atmosphere.

20 Claims, 8 Drawing Sheets

ULTRASONICALLY ACTUATED NEEDLE PUMP SYSTEM

This invention was made with United States government support awarded by the following agency: NSF Grant No: 9632527. The United States has certain rights in this invention.

FIELD OF THE INVENTION

This invention pertains generally to the field of surgical instruments and similar devices, to micromechanical systems, and to ultrasonically actuated instruments.

BACKGROUND OF THE INVENTION

Various types of hypodermic needles have been developed for the injection of substances, e.g., drugs, into the body, or the withdrawal of body fluid samples, e.g., blood. For drawing blood samples from a vein, the subject's blood pressure may be sufficient to pump the blood sample through the bore of the hypodermic needle to a container. In situations where a needle is used to withdraw samples of other body fluids, it is generally necessary to use some type of mechanism to draw or pump the body fluid through the needle to a container, for example, a plunger attached to the needle which can be manipulated to provide a sufficient vacuum draw on the needle to draw the fluid sample through the bore of the needle into the container of the plunger.

While conventional hypodermic needles that can be manipulated by hand by medical personnel have been successfully used for many years for withdrawing relatively large samples of blood and other body fluids, the use of such needles is, of course, accompanied by some tissue damage as the needle punctures the skin and subdermal tissues of the subject. This incidental tissue damage becomes particularly a problem if repeated sampling is required, for example, for monitoring of blood sugars by diabetics or in other situations where it is desirable to be able to closely monitor the levels of blood components or drug levels within a patient. Efforts have thus been directed to the development of miniaturized needle systems which are capable of very lightly puncturing the skin, and in some cases limiting penetration to the dermal layer of skin to collect interstitial fluid in the dermal layer without puncturing capillaries beneath the dermal layer. Examples of such systems are shown in, e.g., U.S. Pat. Nos. 5,582,184, 5,682,233, 5,746,217 and 5,820,570. The small size of the needles and the small amounts of interstitial fluids that are withdrawn through the needle complicate the problem of drawing fluids through the needle to a sample container or a sample chamber.

It has been found that ultrasonically actuated needles will pump fluid from the distal end of the needle to its proximal end under appropriate conditions. Such needles can also be fabricated using microelectromechnical fabrication techniques. See, A. Lal, et al., "Silicon Micro-Fabricated Horns for Power Ultrasonics," Transducers 95, June 1995, Stockholm, Sweden; A. Lal, et al., "Micromachined Silicon Ultrasonic Needle," IEEE Ultrasonics Symposium, Nov. 7–10, 1995, Seattle, Wash., U.S.A.; and U.S. Pat. Nos. 5,569,968 and 5,728,089 to Lal, et al. A limitation of the use of such ultrasonically actuated needles for body fluid sampling is the potential damping of the vibration of the needle as it is inserted into relatively stiff skin tissue. The damping of the vibrations of the needle by skin tissue reduces the efficiency of pumping of fluid from the needle. Further, increasing the amplitude of the vibrations applied to the needle to overcome the loss of efficiency may result in excessive disruption of the body tissue penetrated by the needle by virtue of the mechanical displacement, cavitation, and localized heating of tissue caused by the vibrations.

SUMMARY OF THE INVENTION

In accordance with the present invention, an ultrasonically actuated needle pump system provides efficient pumping of body fluids with minimal disruption of body tissue adjacent to the needle. Ultrasonic pumping action occurs through the needle system without interference with the pumping action by the skin or other body tissue which is penetrated. The needle system is well-suited to the extraction of precisely controlled amounts of fluid for purposes such as sampling of interstitial fluid.

The needle pump system of the invention includes an outer, stationary tubular needle having a distal end, which may have a penetrating tip, and a hollow bore. An inner tubular needle is mounted in the bore of the outer needle. The inner and outer needles may be formed as any type of elongated hollow structure acting as a conduit for fluid, and may have any desired cross-sectional shape in addition to the common round inner and outer surfaces for such conduits. The distal end of the inner tubular needle is located adjacent to, at or spaced slightly away from, the distal end of the outer needle. An ultrasonic actuator is coupled to the inner tubular needle at a position away from the distal end to selectively drive the inner needle in longitudinal mode vibrations at ultrasonic frequencies. The inner needle is free to vibrate independently of the outer needle, and the outer needle is not vibrated and is essentially stationary. The outer needle may, for example, be formed of metal in a conventional fashion with a sharp, penetrating tip, and the inner tubular needle may be formed of a capillary tube which may be formed of a transparent material, such as glass, which facilitates inspection of the contents of the inner needle as it is pumped therethrough. It is found that, in accordance with the invention, the vibration of the inner tubular needle results in highly efficient pumping of fluid from the distal end of the needle system, e.g., at the penetrating tip of the outer needle, to the proximal end opening of the inner tubular needle. Such pumping action occurs when the distal end of the needle system is inserted into a sample of liquid by itself as well as when the needle system is used to penetrate skin tissue. Because the outer needle is stationary, it does not mechanically disrupt or heat the adjacent body tissue, and the surrounding outer needle shields the vibrating inner needle from contact with body tissue so that no damping of the vibrations of the inner needle occurs.

It is also found in accordance with the invention that the needle system of the invention may be utilized to pump fluid from a container at the distal end and to efficiently atomize the liquid at an open proximal end of the inner needle.

Further objects, features and advantages of the invention will be apparent from the following detailed description when taken in conjunction with the accompanying drawings.

DETAILED DESCRIPTION OF THE INVENTION

Figures 1, 2:
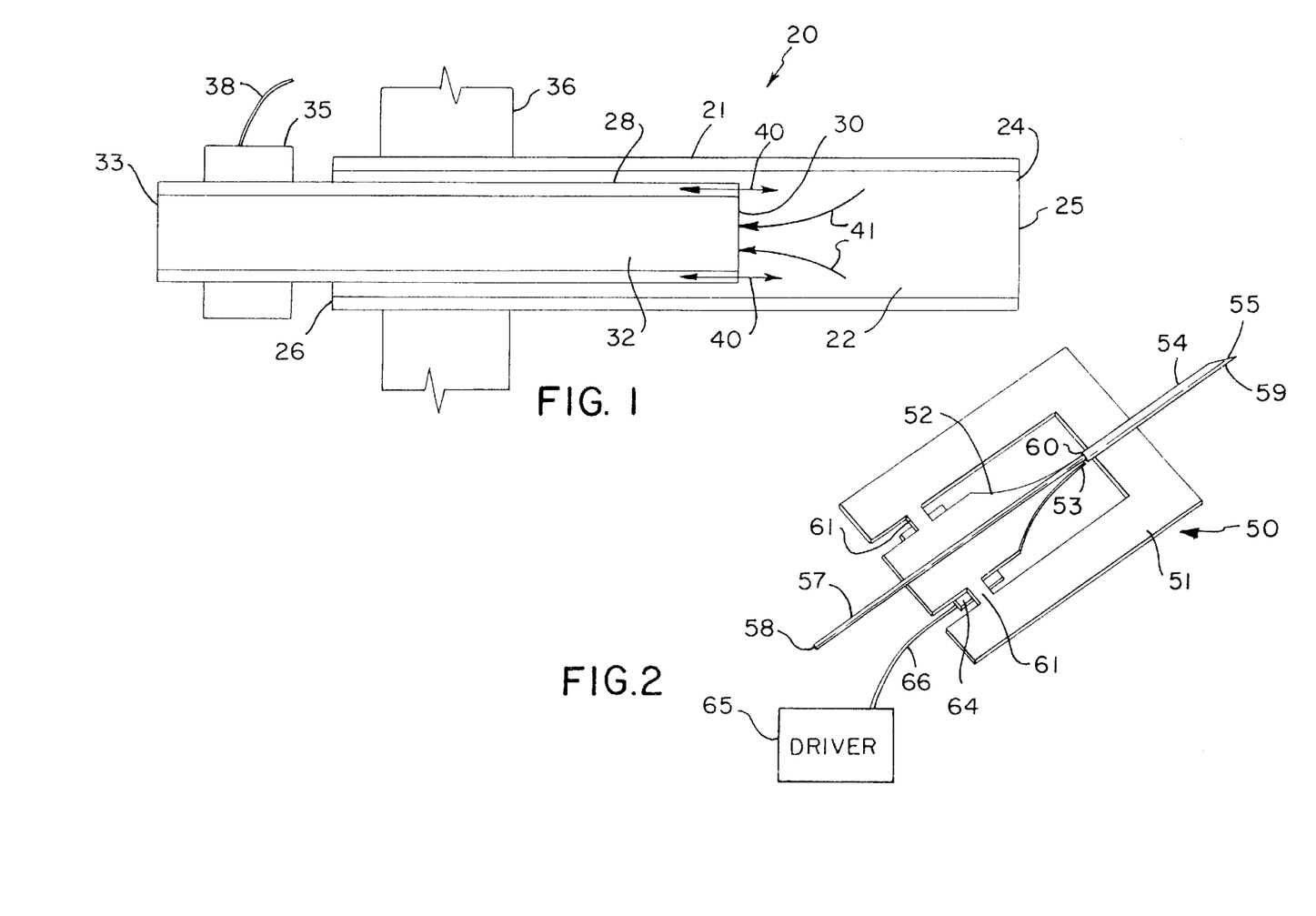
FIG. 1 is a simplified cross-sectional view of an ultrasonically actuated needle pump system in accordance with the invention.
FIG. 2 is a perspective view of an ultrasonically activated needle pump system in accordance with the invention.

A simplified cross-sectional view of an ultrasonically actuated needle pump for fluid sampling or atomization in accordance with the invention is shown generally at 20 in FIG. 1. The ultrasonic pump includes an outer tubular needle 21 having an inner bore 22, which may be circular as shown, a distal end 24 which has an end opening 25 that may be formed blunt as shown (or the opening may be cut on a bias to form a penetrating tip), and a proximal end 26. A tubular inner needle 28 is mounted within the bore 22 of the outer needle 21 and is not secured to the surfaces of the bore 22 so that it can move longitudinally without substantial interference from the outer tubular needle 21. The inner tubular needle 28 has a distal end 30 which, as shown in FIG. 1, is adjacent to but preferably spaced from the distal end 24 of the outer tubular needle 21. Preferably, the distal end 30 of the inner needle is spaced from the distal end 24 of the outer needle by a distance in the range of a fraction of a millimeter to a few millimeters. The inner needle 28 also has an inner circular bore 32 and a proximal end 33. The proximal end 33 may be left open, as shown FIG. 1, for atomization, or may be connected to a sampling device or a container for the fluid to be pumped through the system. An ultrasonic actuator 35 is coupled to the inner tubular needle 28 to apply ultrasonic vibrational energy thereto, but, as illustrated in FIG. 1, is out of contact with the outer needle 21 so that it does not vibrate the outer needle. The outer needle 21 is mounted to a base 36 which holds the outer needle stationary. To provide structural support to the ultrasonic actuator 35 and to the inner tubular needle 28, the needle 28 and the actuator 35 may be mounted to the base 36 or to other structures (not shown) in a manner which allows the ultrasonic actuator and the inner needle 28 to vibrate freely without vibrating the outer needle 21. The ultrasonic actuator 35 may be, for example, a piezoelectric actuator which is provided with drive power through wires 38.

When power is supplied to the ultrasonic actuator 35 to vibrate the inner needle 28 in longitudinal mode vibrations, illustrated by the lines 40 in FIG. 1, the vibrating needle 28 creates a gradient of acoustic energy which decreases away from the needle 28. This gradient results in a net momentum transfer towards the inner needle 28, resulting in the pumping of liquid. This phenomenon is also sometimes referred to as acoustic streaming. The result is the drawing in of fluids through the opening 25 at the distal end 24 of the outer needle and thence into the opening at the distal end 30 of the inner tubular needle 28, as illustrated by the streaming lines 41 in FIG. 1. Generally, the mechanical system comprised of the inner tubular needle 28 and the ultrasonic actuator 35 will exhibit acoustic resonances and the maximum pumping action generally occurs when the ultrasonic actuator 35 is provided with power at a frequency that drives the inner tubular needle 28 to vibrate at resonance. As illustrated in FIG. 1, the outer diameter of the inner needle 28 is smaller than the inner diameter of the outer needle 21 so that the inner needle can vibrate freely without excessive contact with the outer needle which might damp the vibrations.

The ultrasonically actuated needle pump system of the invention is particularly advantageous in the extraction of interstitial fluid. Interstitial fluid in skin has major lymph-related metabolite molecules which are filtered across the capillary walls from blood in the capillaries. A major advantage of sampling interstitial fluid is the minimal degree of invasive penetration of tissue, typically requiring penetration only 100 to 500 microns beneath the skin surface, which minimizes pain and the risk of infection. The needles 21 and 28 of the present invention can be fabricated in small sizes, adapted for low voltage driving, which are well-suited to portable interstitial sampling units. It is also understood that the ultrasonic actuated pump of the present invention can be used in the reverse direction to deliver drugs into the skin from a drug supply at the proximal end of the inner tubular needle by appropriate arrangement of the outer and inner needles and choice of ultrasonic drive actuator frequency.

The present invention can be fabricated in a variety of ways using various materials. The inner and outer needles may be formed of tubes of various materials such as metals, glass, and silicon. Silicon based devices can be formed as described in the above referenced patents and publications by Lal, et al. An example of an ultrasonic actuated pump system in accordance with the present invention that is well-suited for interstitial sampling is shown at 50 in FIG. 2. The pump 50 is formed of an outer silicon base frame 51, a silicon horn 52 for concentrating ultrasonic energy at the tip 53 thereof, an outer (hypodermic) needle 54 having a penetrating tip 55 at its distal end and preferably formed of metal (e.g., stainless steel), and an inner tubular needle 57 which may be, for example, a glass capillary tube having a hollow bore, with a proximal end 58 and a distal end adjacent to the distal end 57 of the outer needle at the position indicated at 59 in FIG. 2. The outer hypodermic needle 54 is bonded to the base frame 51, e.g., by utilizing an adhesive such a cyanoacrylate. The inner capillary tube needle 57 extends out of the proximal end 60 of the outer tube 54 and is bonded, e.g., with cyanoacrylate, to the silicon horn 52. The silicon horn 52 is connected to and supported by the outer frame 51 by bridge connectors 61 which essentially allow the horn 52 to be vibrationally isolated from the frame 51. The bridge connectors are preferably joined to the horn 52 at the position of a vibrational node of the horn to minimize transmission of vibrations through the base 51 to the outer needle 54. As indicated below, the horn 52, the connectors 61, and the outer frame 51 may be formed from a unitary piece of silicon by conventional silicon machining techniques. An ultrasonic actuator 64, e.g., a lead-zirconate-titanate (PZT) piezoelectric ceramic, is bonded to the silicon horn 52, for example, by using a glue such as cyanoacrylate. An ultrasonic driver 65 is connected by wires 66 to the piezoelectric actuator 64 to provide oscillatory electrical power thereto, typically in the frequency range of 100 KHz to 1 MHz or higher. Exemplary dimensions for the device of FIG. 2 include a base frame 51 of 1.6 cm by 1.5 cm, an inside diameter of the bore of the inner needle 57 of 40 micrometers and an outside diameter of the inner needle of 150 micrometers, and for the outer needle 54 an inside bore diameter of 400 micrometers and an outside diameter of 600 micrometers. If desired, another ultrasonic actuator (not shown) could be bonded to the base 51 to selectively vibrate the base and the outer needle 54. The outer needle 54 could be vibrated, for example, during initial penetration of the tip 55 into the skin or to pump liquid through the bore of the outer needle for discharge at the proximal end 60 of the outer needle.

Figure 3:
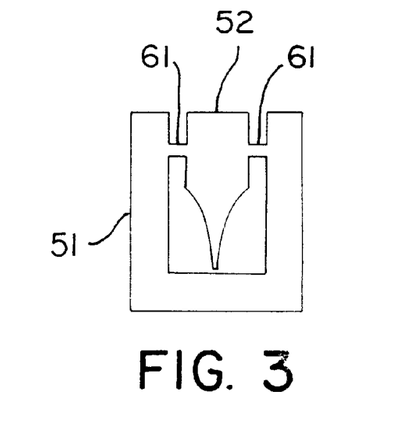
FIG. 3 is a plan view of the silicon base frame structure for the ultrasonically activated needle pump system of FIG. 2.
Figure 4:
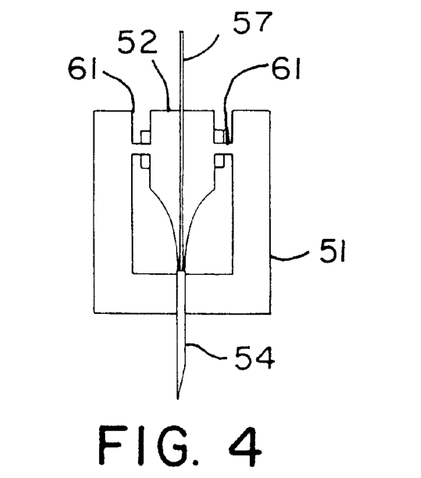
FIG. 4 is a plan view of the ultrasonically actuated needle pump system of FIG. 2 showing the inner and outer tubular needles mounted to the base frame shown in FIG. 3.
Figure 5:
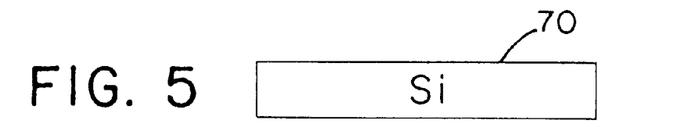
FIGS. 5–8 are simplified cross-sectional views illustrating the steps in the fabrication of the silicon base frame of FIG. 3.
Figure 6:
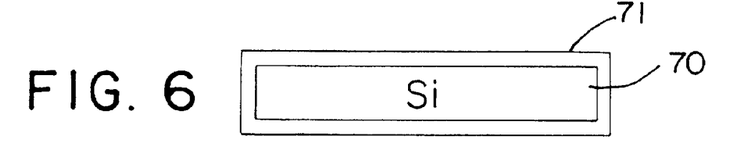
Figure 7:
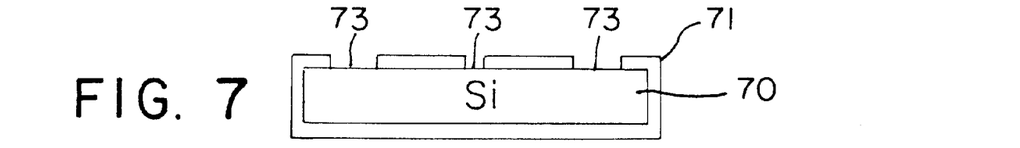
Figure 8:
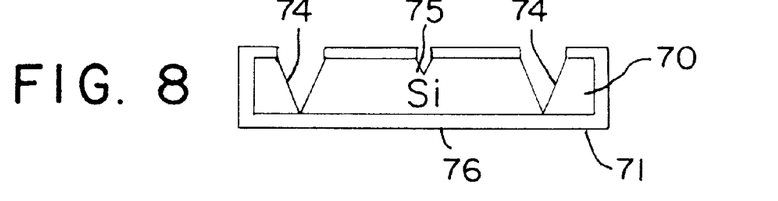

The ultrasonically actuated pump system 50 of FIG. 2 may be fabricated in part using silicon processing techniques. A first step in the fabrication of the device of FIG. 2 involves the patterning and etching of the base frame 51 and the horn section 52 from a single piece of crystalline silicon, as illustrated in FIG. 3. Grooves are then etched in the horn section 52 and in the base frame 51 to mount the outer needle 54 to the base 51 and the inner capillary tube needle 57 to the horn section 52 in proper alignment with one another, as illustrated in FIG. 4. For example, the base frame 51 and horn section 52, with connectors 61, may be fabricated from a three inch <100> p-type silicon wafer 70, as illustrated in FIG. 5, on which was deposited a film 71 of 0.7 micron LPCVD (low pressure chemical vapor deposition) silicon nitride as shown in FIG. 6. The silicon nitride layer was then patterned to outline the desired shape of the structure shown in FIG. 3 and was etched by plasma etching to expose the silicon in appropriate positions 73 as shown in FIG. 7. Anisotropic etching using KOH was then carried out for 8 hours at 80° C., to result in the etched areas 74 and the groove 75 as illustrated in FIG. 8. The PZT plate 64 was then bonded to the bottom side 76 of the horn section 52 using cyanoacrylate glue. The PZT plate size was 12 mm×6 mm, with a thickness of 0.7 mm. The outer hypodermic needle 54 was then placed in and secured in the groove 75 formed in the frame 51 using cyanoacrylate, and the inner capillary tube needle 57 was then inserted into the outer hypodermic needle 54 until its distal end was close to the tip of the needle 54, and the inner needle 57 was then placed in the groove 75 in the horn section 52 and glued in place to the horn using cyanoacrylate glue.

Figure 9:
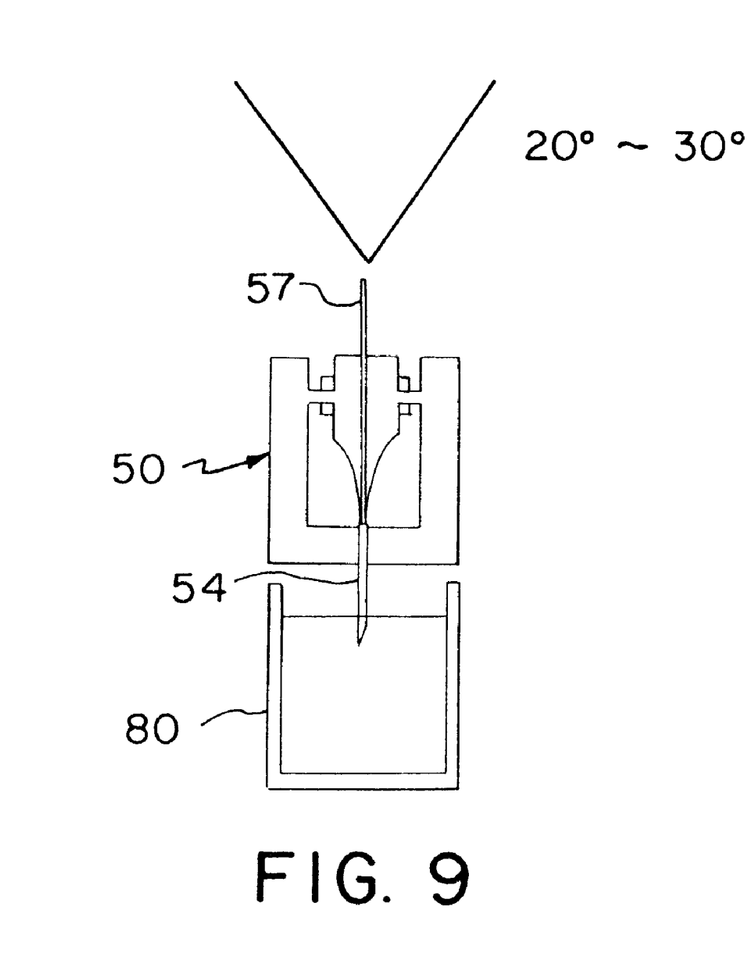
FIG. 9 is an illustrative view showing the ultrasonically actuated needle pump system of FIG. 2 used to pump and atomize water.
Figure 10:
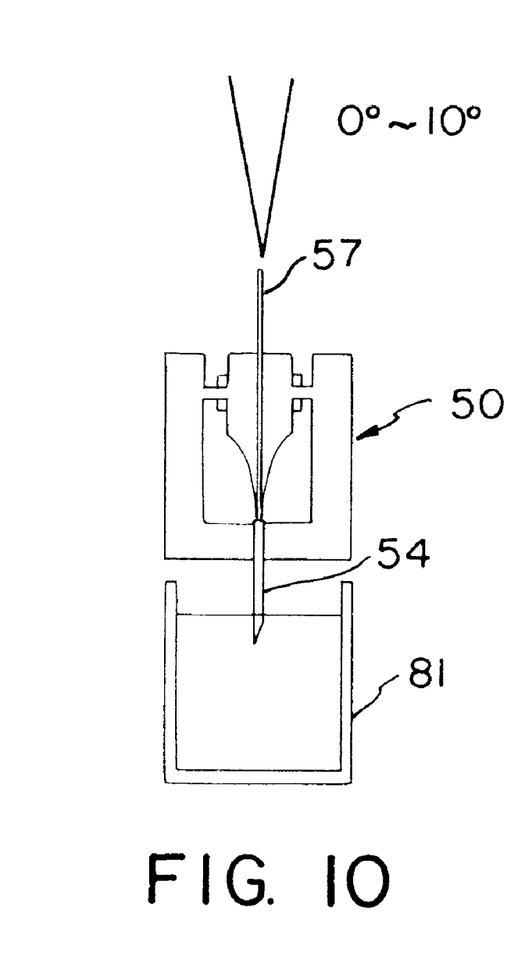
FIG. 10 is an illustrative view of the ultrasonically actuated needle pump system of FIG. 2 used to pump and atomize ethyl alcohol.
Figure 11:
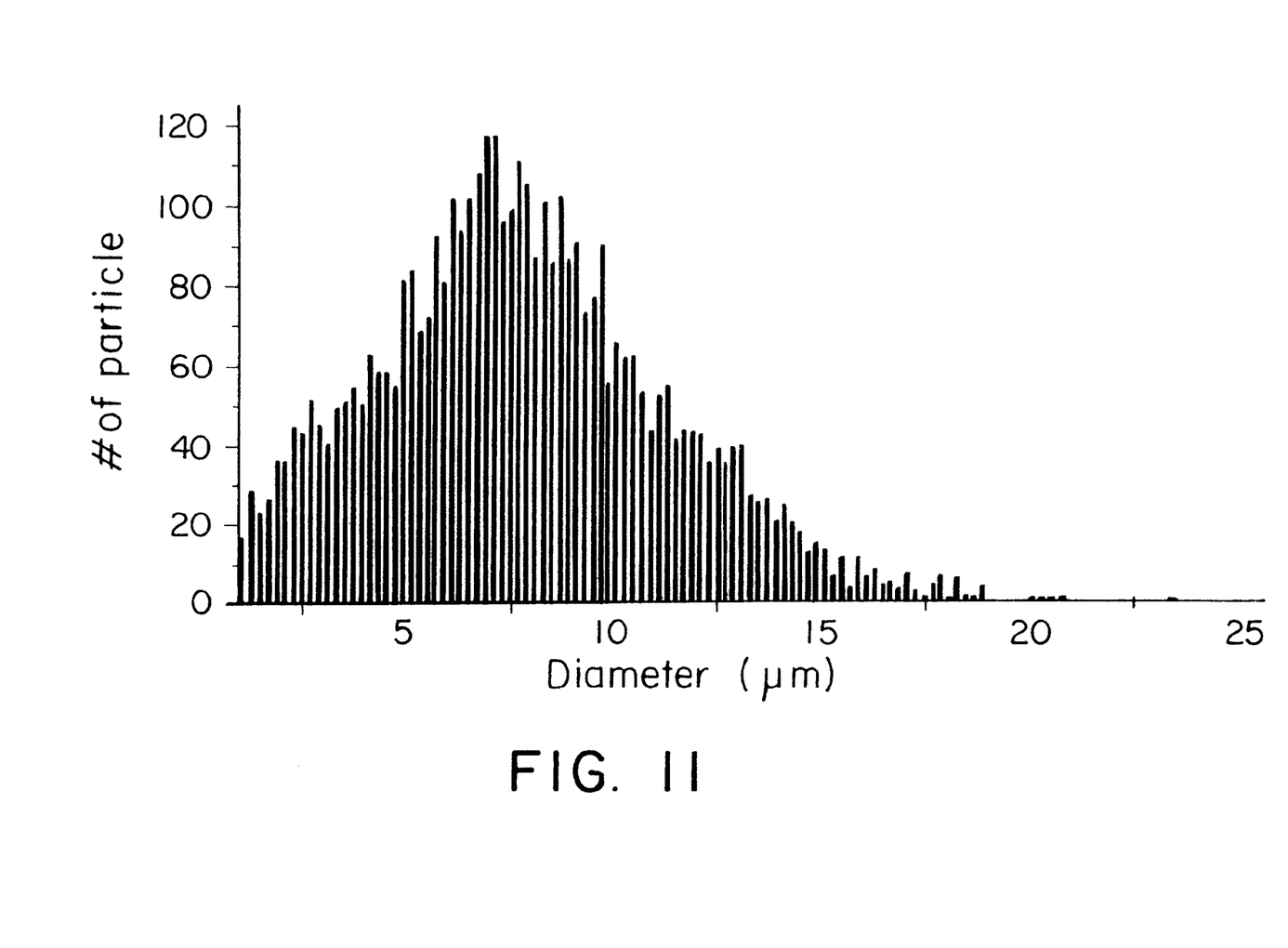
FIG. 11 is a graph showing the atomized particle size distribution for the ultrasonically actuated needle pump system of FIG. 2.
Figure 12:
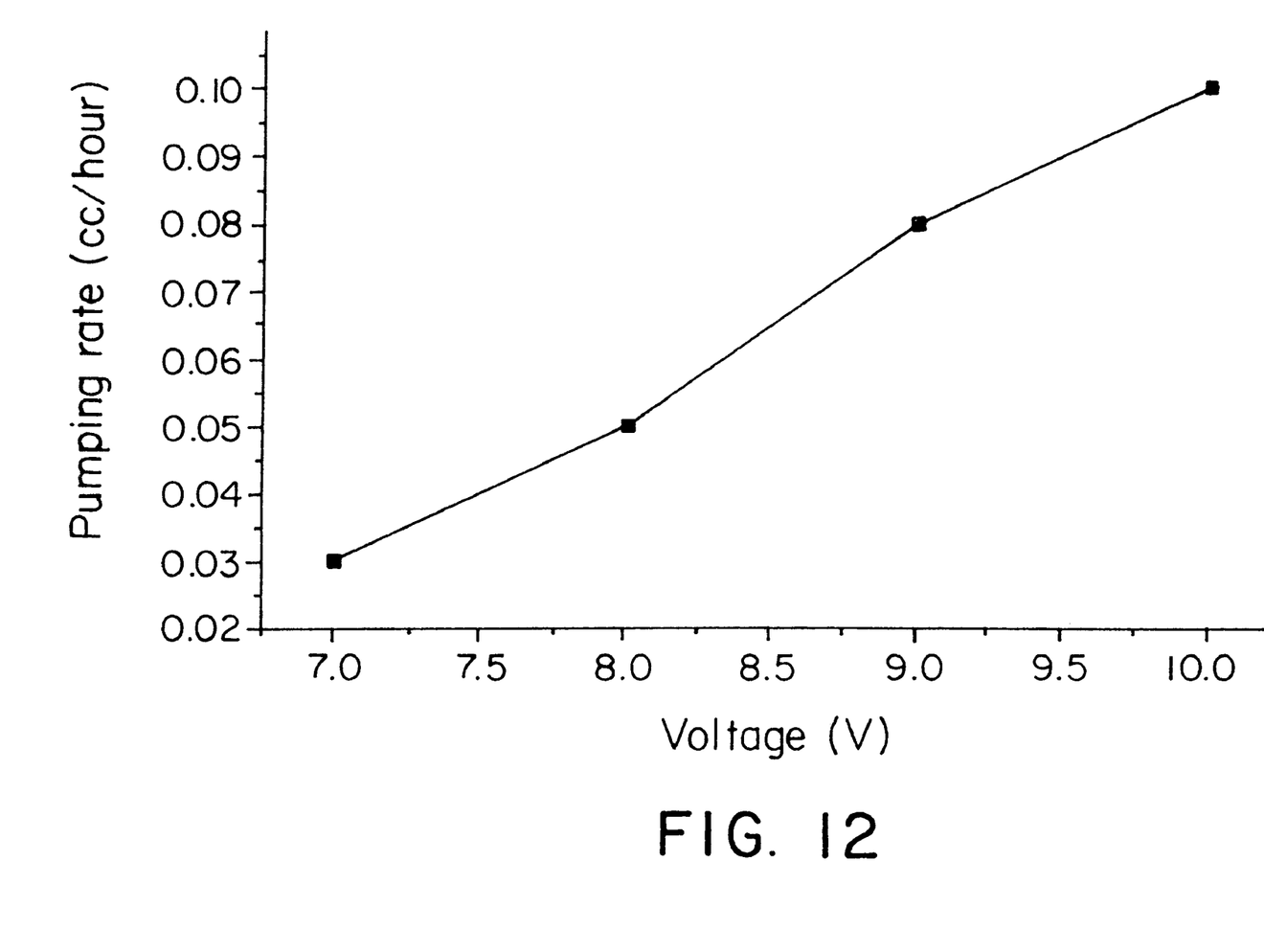
FIG. 12 is a graph illustrating the pumping rate of water for the ultrasonically actuated needle pump system of FIG. 2 as a function of the voltage applied to the ultrasonic actuator.

The foregoing pump structure was used to pump liquids from the distal end 55 to the proximal end 58, with atomization found to take place when the proximal end 58 is open to the atmosphere. The resonant frequencies of the ultrasonically vibrated system formed of the needle 57, horn 52, and actuator 64 were determined utilizing electrical impedance measurements, and several resonant frequencies, corresponding to different structural resonance modes, were found to exist. The resonant operation results in large motion at the distal end 59 of the inner needle, resulting in efficient pumping. The frequency of most efficient pumping of water was found to be at 625 KHz. Other resonant frequencies occurred at 456 KHz and 920 KHz, but with less reliable or stable pumping. To test the characteristics of the pump, two different liquids, water and ethyl alcohol, were pumped to determine differences in pumping action for the different types of liquid. It is understood that other liquids, such as perfume, will also be efficiently pumped by this type of pump system. As illustrated in FIG. 9, when water was pumped from a container 80, the angle of atomization of droplets exiting from the proximal end of the inner needle 57 was in the range of 20° to 30°. As illustrated in FIG. 10, when ethyl alcohol was pumped from a container 81, the angle of atomization of droplets exiting from the proximal end of the inner needle 57 was in the range of 0° to 10°. In addition, the rate of pumping of water was found to be higher than that for ethyl alcohol, which correlates to the fact that the viscosity of water is less than that of ethyl alcohol. The sizes of the water droplets atomized from the proximal end of the inner needle were measured by laser scattering, with 8 microns being found to be the average size of the droplets measured. The particle size distribution for the measured droplets is illustrated in FIG. 11. A water reservoir was used to measure the pumping rate. The ultrasonic pump 50 was driven to pump and atomize water at different applied voltages ranging from 7 to 10 volts peak-to-peak at a resonance frequency of 625 KHz for one hour. The pumping rate versus supplied power had a linear relationship, as illustrated in FIG. 12.

Figure 13:
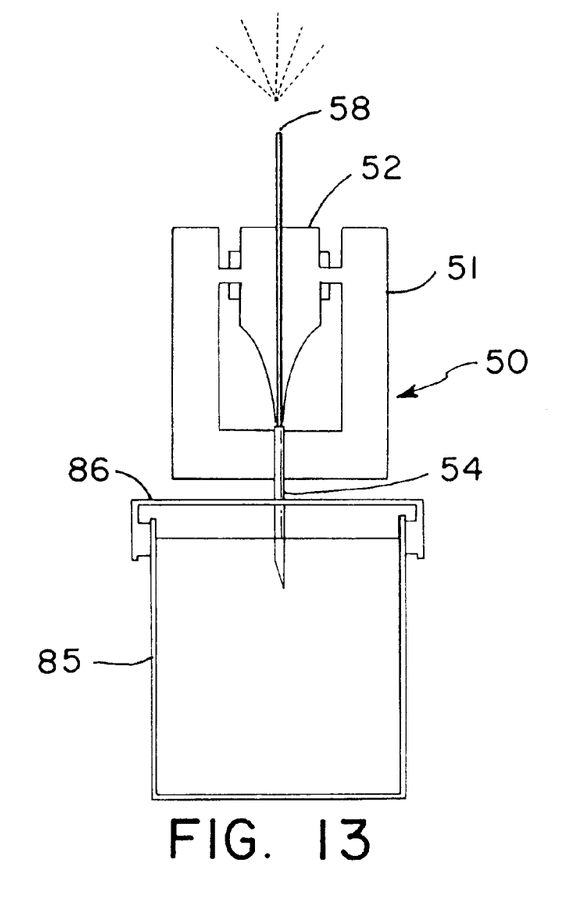
FIG. 13 is an illustrative view showing the needle pump system of FIG. 2 penetrating a membrane to pump the liquid in the container beneath the membrane.

A particular advantage of the ultrasonic pump of the present invention is that the high efficiency of pumping through the needle is not degraded by contact of the needle with skin or other body tissue. Because the stationary outer needle 21 is in contact with the skin and shields the vibrated inner needle 28 from such contact, no substantial damping of the vibrational resonance of the inner needle 28 occurs. The action of the needle system upon insertion into tissue can be simulated as shown in FIG. 13, in which a plastic container 85, filled with water, is capped by a 0.5 mm thick rubber membrane 86 that simulates the skin of an animal subject. The hypodermic needle 54 was pressed against and punctured the rubber membrane 86 and was advanced into the water held in the container 85. The system was found to pump water from the container 85 and atomize the water at the proximal exit end 58 at an applied voltage of 10 volts peak-to-peak at the same resonance frequency, 625 KHz, at which resonance and maximum pumping occurred for the needle system 50 with the outer needle 54 in contact only with water.

The ability of the ultrasonically acatuated needle pump of the present invention to efficiently pump liquid from the distal end to the proximal end is believed to be due to two pumping mechanisms. A first is acoustic streaming inside the space in front of the inner needle and inside the outer needle. The ultrasonic motion induces a toroidal motion of liquid. This steady state motion of fluid, even though the actuation is at a high frequency, is a result of the nonlinear acoustic streaming phenomenon. The nonlinear connective part of the Navier-Stokes equation, which governs fluid motion, produces a steady state time-averaged force in the presence of sinusoidal pressure waves. This phenomenon has been described in e.g., Bradley, C. E., "Acoustic streaming field structure: the influence of the radiator," *J. Acous. Soc. Am.*, September 1996, vol. 100, no.3, pp. 1399–408; and Jackson, F. J., et al., "Sonically-induced microstreaming near a plane boundary. I. The sonic generator and the associated acoustic field," *J. Acous. Soc. Am.*, vol. 32 no. 10, October 1960, pp. 1243–1250. Acoustic streaming has been analyzed for vortex generation from a rigid piston. See, e.g., Jackson, F. J., "Sonically-induced micro-streaming near a plane boundary. II. Acoustic streaming field," *J. Acous. Soc. Am.*, vol. 32, no. 11, November 1960, pp. 1387–1395; and Nyborg, W. L., "Acoustic streaming," in *Physical Acoustics* (W. P. Mason, ed.), vol. 2B, Academic Press, New York, N.Y., 1949, pp. 1415–1422.

In the present invention vortices are observed but the positive pressure at the center of the toroidal vortex results in pumping the liquid. While vortex generation and pumping occurs even for a single needle, the outer needle focuses the acoustic field inside the outer needle and results in a much more active vortex. The outer needle also forms an acoustic resonator between the active inner capillary needle and the adjacent orifice of the outer needle. An acoustic impedance exists at the faces at the distal ends of both the outer and inner needles. This effective impedance results in a buildup of acoustic intensity inside the resonator. This has been seen as an effective higher pumping force when the distance between the driving inner capillary distal end and the outer needle distal end is tuned to be one wavelength or half wavelengths in the liquid.

In addition to the acoustic streaming generated vortex due to the acoustic field induced in front of the inner capillary tube, there also exists a shear field in the liquid on side surfaces of the needles. The needle walls shear the fluid surrounding them while pushing the liquid in front of it. The shear field decays exponentially in a characteristic length called the shear viscous depth. An expression for this depth is $$\delta = \sqrt{\frac{v}{\pi f}}$$

where v is the kinematic viscosity and f is the frequency of the ultrasonic field. The shear viscous depth for water ranges from less than a micron to a couple of microns in the frequency range of 100 KHz to 1 MHz for water. The time averaged acoustic streaming force in the shear field results in a steady movement of the flow as well. This is believed to be a secondary effect in pumping of the fluid on the surface wall of the inner capillary.

Another possible explanation for pumping is ultrasonic cavitation induced higher average pressure in front of the driving needle. However, in the present invention intensities may be used (~0.1 W/cm$^2$) that are much lower than what is needed for cavitation at the frequencies of ~500 KHz. Cavitation is believed to be nearly negligible at frequencies above 100 kHz.

Figure 14:
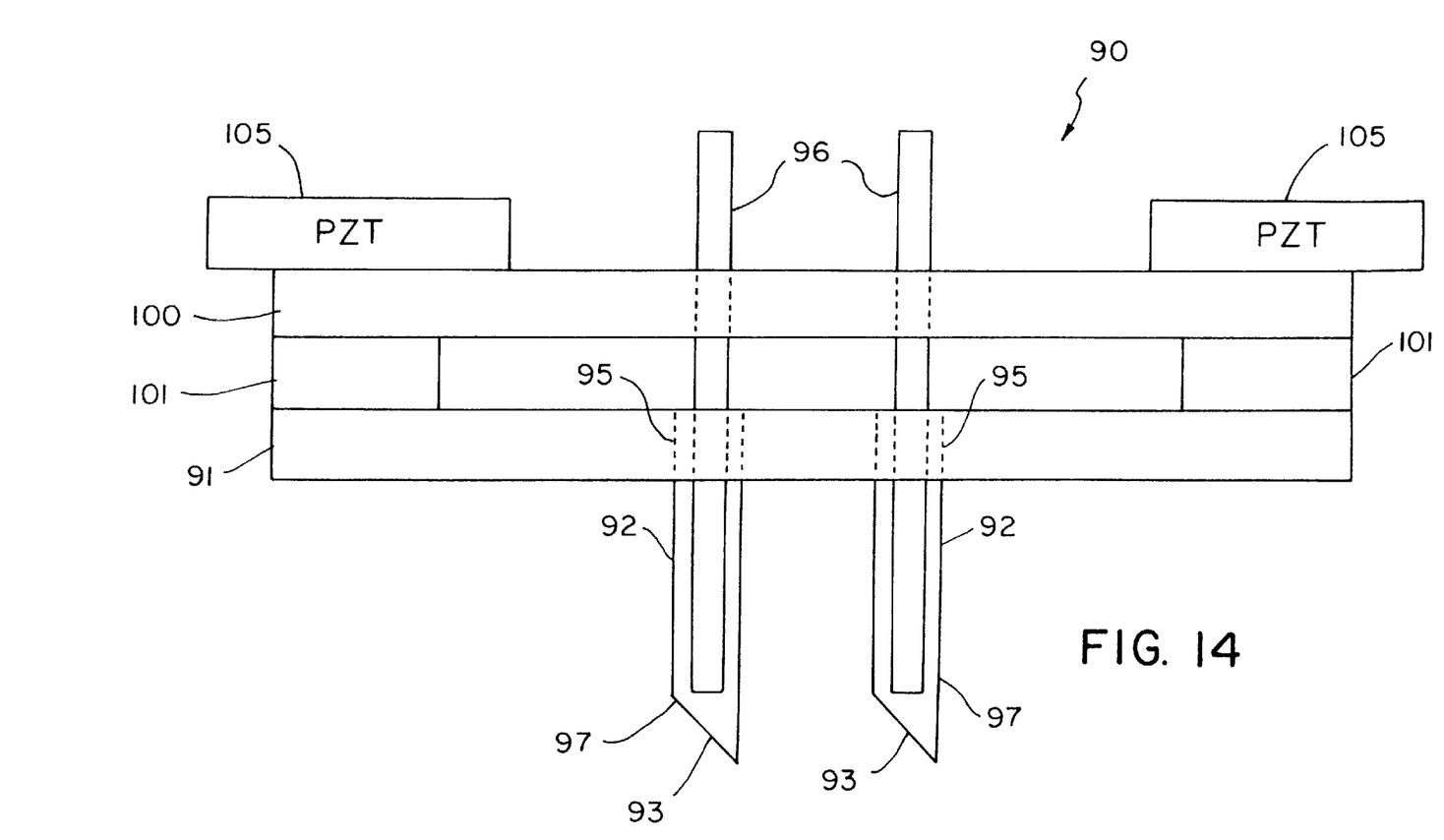
FIG. 14 is a simplified cross-sectional view of a needle pump system array in accordance with the invention.
Figure 15:
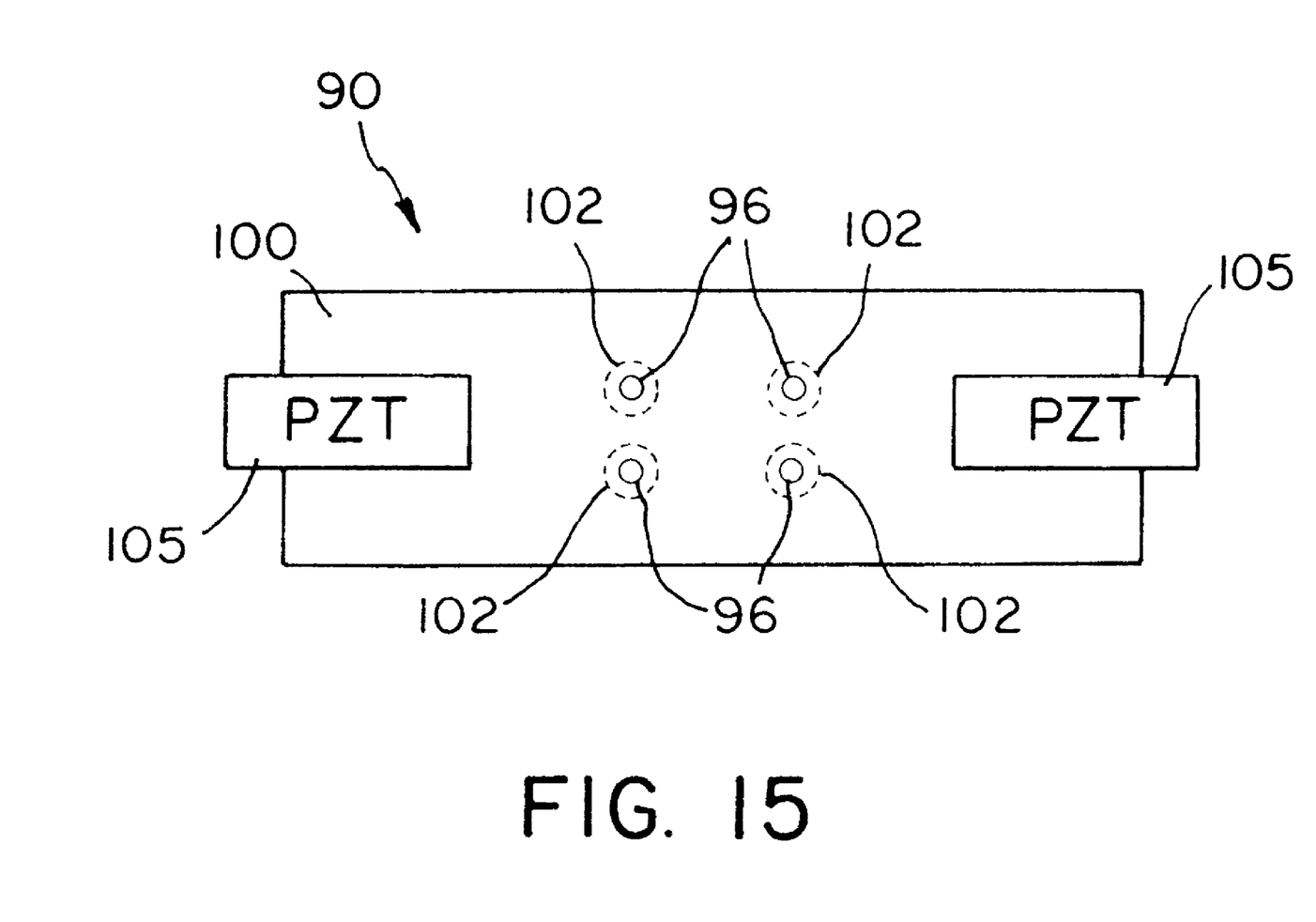
FIG. 15 is a plan view of the needle pump system array of FIG. 14.

As noted above, the present invention is particularly well suited to use in sampling interstitial body fluid obtained from the dermal layer of tissue, in which only slight penetration of the skin is required. To facilitate control of the depth of penetration into the skin and to increase the amount of fluid drawn for analysis, the present invention may be embodied in a needle array based pumping apparatus, as illustrated generally at 90 in a side view in FIG. 14 and in a top view in FIG. 15. The pumping apparatus 90 includes a lower mounting plate 91 (e.g., of stainless steel), to which an array of outer hypodermic needles 92 having penetrating tips 93 at their distal ends are fixed, e.g., by tapping tightly into holes 95 in the mounting plate 91. Hollow inner needle tubes 96 are inserted into the bores of the outer needles 92, each inner needle having a distal end 97 which is preferably positioned spaced from, but closely adjacent to the penetrating tip 93 of the outer hypodermic needle tube 92. An upper vibration transmitting plate 100 (e.g., of stainless steel) is mounted to the lower plate using spacers 101 formed of, e.g., silicon. The spacers 101 secure the two plates 91 and 100 together but reduce vibrational coupling between the two plates since only the upper plate 100 is to be vibrated during pumping. In addition, the spacers 101 can also be vibrational actuators, such as PZT plates, so that drive power can be supplied to such actuators to vibrate the outer needles 92, to facilitate initial penetration into the skin, after which such actuators are turned off during ultrasonic pumping. The capillary-like inner needles 96 are passed through holes 102 in the upper plate 100 and into the bores of the outer hypodermic needles 92. The inner capillary tube needles 96 are adhesively attached to the upper plate at the holes 102 by, e.g., cyanoacrylate so that the inner needles will be vibrated by the upper plate. Exemplary dimensions for the holes 95 in the lower plate 91 and the holes 102 in the upper plate 100 (which may be formed by electrical discharge machining) are 300 micrometers and 100 micrometers, respectively. Ultrasonic actuators 105 comprising PZT plates are then adhesively mounted onto the upper surface of the upper plate 100, e.g., with cyanoacrylate. The two actuators 105 are mounted to the plate to provide a bimorph structure. Each of the plates 105 can be driven by a separate ultrasonic driver. The power applied to the two piezoelectric actuators 105 is provided at voltage levels and frequencies that are found to provide an appropriate resonance of the plate and inner needle structure and to yield the desired pumping action of liquid through the inner capillary tube needles 96.

It is understood that the invention is not confined to the particular embodiments set forth herein as illustrative, but embraces all such modifications thereof as come within the scope of the following claims.

What is claimed is:

1. An ultrasonically actuated pump comprising:
   (a) an outer needle having a distal end and a hollow bore;
   (b) an inner needle having a hollow bore mounted within the bore of the outer needle and having a distal end positioned adjacent to and spaced inwardly from the distal end of the outer needle and a proximal end; and
   (c) an ultrasonic actuator, coupled to the inner needle to selectively apply ultrasonic vibrations thereto without vibrating the outer needle.

2. The ultrasonically actuated pump of claim 1 wherein the distal end of the outer needle is cut at a bias to form a skin penetrating tip.

3. The ultrasonically actuated pump of claim 1 further including a base to which the outer needle is fixed, and supports coupling the inner needle to the base without transmission of vibrations from the inner needle through the base to the outer needle.

4. The ultrasonically actuated pump of claim 1 wherein the ultrasonic actuator comprises a piezoelectric transducer.

5. The ultrasonically actuated pump of claim 4 wherein the piezoelectric transducer comprises a PZT ceramic plate.

6. The ultrasonically actuated pump of claim 1 wherein the outer needle is a tube of a material selected from the group consisting of a metal, glass, and silicon, and the inner needle is a capillary tube of a material selected from the group consisting of glass, metal, and silicon.

7. An ultrasonically actuated pump comprising:
   (a) an outer needle having a distal end and a hollow bore, wherein the outer needle comprises a penetrating tip;
   (b) an inner needle having a hollow bore mounted within the bore of the outer needle and having a distal end positioned adjacent to the distal end of the outer needle and a proximal end;
   (c) an ultrasonic actuator, coupled to the inner needle to selectively apply ultrasonic vibrations thereto without vibrating the outer needle; and
   (d) a silicon base to which the outer needle is fixed, and a silicon horn formed to concentrate ultrasonic energy at a tip of the horn, wherein the inner needle is bonded to the silicon horn to vibrate therewith, and wherein the ultrasonic actuator is bonded to the silicon horn, such that actuation of the ultrasonic actuator drives vibrations in the silicon horn which are transmitted to the inner needle bonded thereto.

8. An ultrasonically actuated pump comprising:

(a) an outer needle having a distal end and a hollow bore, wherein the outer needle comprises a penetrating tip;

(b) an inner needle having a hollow bore mounted within the bore of the outer needle and having a distal end positioned adjacent to the distal end of the outer needle and a proximal end;

(c) an ultrasonic actuator, coupled to the inner needle to selectively apply ultrasonic vibrations thereto without vibrating the outer needle; and (d) a silicon base to which the outer needle is fixed, and a silicon horn formed to concentrate ultrasonic energy at a tip of the horn, wherein the inner needle is bonded to the silicon horn to vibrate therewith, and wherein the ultrasonic actuator is bonded to the silicon horn, such that actuation of the ultrasonic actuator drives vibrations in the silicon horn which are transmitted to the inner needle bonded thereto;

wherein the silicon base and the silicon horn are formed from a unitary piece of crystalline silicon and are joined together by connectors extending between the base and the silicon horn at a node of vibration in the silicon horn so that vibrations of the horn are not substantially transmitted to the base.

9. The ultrasonically actuated pump of claim 1 wherein the proximal end of the inner needle is open to the atmosphere so that liquid pumped from the distal end of the inner needle to its proximal end is atomized into the atmosphere at the proximal end.

10. The ultrasonically actuated pump of claim 1 wherein the outside diameter of the outer needle is less than or equal to about 600 micrometers.

11. The ultrasonically actuated pump of claim 1 wherein the ultrasonic actuator is a piezoelectric transducer, and further including an electrical power driver connected to supply oscillating electrical power to the piezoelectric transducer.

12. An ultrasonically actuated pump comprising:

(a) a plurality of parallel outer needles mounted together to a mounting plate, each outer needle having a hollow bore and a distal end at a position spaced away from the mounting plate;

(b) a plurality of inner needles, each inner needle mounted within the bore of an outer needle and free to vibrate with respect to the outer needle, each inner needle having a hollow bore, a proximal end, and a distal end positioned adjacent to the distal end of the outer needle in which it is mounted;

(c) an ultrasonic actuator coupled to the inner needles to selectively vibrate the inner needles at ultrasonic frequencies without vibrating the outer needles.

13. The ultrasonically actuated pump of claim 12 wherein each of the inner needles are secured to a vibration transmitting plate, and wherein the ultrasonic actuator is at least one piezoelectric transducer bonded to the vibration transmitting plate to transmit vibrations therethrough to the inner needles.

14. The ultrasonically actuated pump of claim 13 further including spacers between the mounting plate for the outer needles and the vibration transmitting plate for the inner needles to secure the two plates together without substantially transmitting vibrations from the vibration transmitting plate to the mounting plate.

15. The ultrasonically actuated pump of claim 12 wherein the distal end of each outer needle is cut at a bias to form a skin penetrating tip.

16. The ultrasonically actuated pump of claim 12 wherein the ultrasonic actuator comprises a piezoelectric transducer.

17. The ultrasonically actuated pump of claim 16 wherein the piezoelectric transducer comprises a PZT ceramic plate.

18. The ultrasonically actuated pump of claim 12 wherein each outer needle is formed of a metal tube and each inner needle is formed of a glass capillary tube.

19. The ultrasonically actuated pump of claim 12 wherein the proximal end of each inner needle is open to the atmosphere so that liquid pumped from the distal end of each inner needle to its proximal end is atomized into the atmosphere at the proximal end.

20. The ultrasonically actuated pump of claim 12 wherein the ultrasonic actuator is a piezoelectric transducer, and further including an electrical power driver connected to supply oscillating electrical power to the piezoelectric transducer.

* * * * *